(12) United States Patent
Schmidt et al.

(10) Patent No.: US 10,713,781 B2
(45) Date of Patent: *Jul. 14, 2020

(54) SYSTEMS AND METHODS FOR DETERMINING REGIONS SUITABLE FOR GAS IMAGING PROCESSES

(71) Applicant: Fluke Corporation, Everett, WA (US)

(72) Inventors: Matthew F. Schmidt, River Falls, WI (US); Tyler B. Evans, Edmonds, WA (US); Derek Hutton, Golden, CO (US)

(73) Assignee: Fluke Corporation, Everett, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/258,173

(22) Filed: Jan. 25, 2019

(65) Prior Publication Data
US 2019/0172192 A1 Jun. 6, 2019

Related U.S. Application Data

(63) Continuation of application No. 15/284,146, filed on Oct. 3, 2016, now Pat. No. 10,217,210, which is a
(Continued)

(51) Int. Cl.
*G01N 21/3504* (2014.01)
*G06T 7/00* (2017.01)
(Continued)

(52) U.S. Cl.
CPC ............ *G06T 7/001* (2013.01); *G01J 3/0289* (2013.01); *G01J 3/10* (2013.01); *G01J 3/2803* (2013.01);
(Continued)

(58) Field of Classification Search
CPC .......... G06T 7/174; G06T 2207/10048; G06T 2207/10036; H04N 5/332; G01N 21/3504; G01N 2021/3155; G01N 2201/0221
(Continued)

(56) References Cited

U.S. PATENT DOCUMENTS

| 5,656,813 A | 8/1997 | Moore et al. |
| 7,189,970 B2 | 3/2007 | Racca et al. |

(Continued)

FOREIGN PATENT DOCUMENTS

JP 2014219795 A 11/2014

OTHER PUBLICATIONS

International Search Report and Written Opinion of the ISA/EP in PCT/US2019/033779, dated Sep. 20, 2019, 24 pgs.
(Continued)

*Primary Examiner* — Que Tan Le
(74) *Attorney, Agent, or Firm* — Fredrikson & Byron P.A.

(57) ABSTRACT

Aspects of the invention generally relate to illumination gas imaging and detection. Camera systems can illuminate a target scene with light sources configured to emit absorbing and non-absorbing wavelengths with respect to a target gas. An image of the target scene illuminated with a non-absorbing wavelength can be compared to a non-illuminated image of the target scene in order to determine information about the background of the target scene. If sufficient light of the non-absorbing wavelength is scattered by the scene toward a detector, the target scene comprises an adequate background for performing a gas imaging process. A camera system can alert a user of portions of the target scene suitable or unsuitable for performing a gas imaging process. If necessary, the user can reposition the system until sufficient
(Continued)

portions of the target scene are recognized as suitable for performing the gas imaging process.

18 Claims, 8 Drawing Sheets

Related U.S. Application Data continuation of application No. 14/310,914, filed on Jun. 20, 2014, now Pat. No. 9,464,984.

(51) Int. Cl.

| | |
|---|---|
| *G01N 21/39* | (2006.01) |
| *H01L 27/146* | (2006.01) |
| *G01N 33/00* | (2006.01) |
| *G01N 21/31* | (2006.01) |
| *G01J 3/02* | (2006.01) |
| *G01J 3/10* | (2006.01) |
| *G01J 3/28* | (2006.01) |
| *G01J 3/42* | (2006.01) |
| *G01S 17/88* | (2006.01) |
| *G01S 17/89* | (2020.01) |
| *G01S 17/00* | (2020.01) |
| *H04N 5/225* | (2006.01) |
| *H04N 5/33* | (2006.01) |

(52) U.S. Cl.
CPC .............. *G01J 3/2823* (2013.01); *G01J 3/42* (2013.01); *G01N 21/3151* (2013.01); *G01N 21/3504* (2013.01); *G01N 21/39* (2013.01); *G01N 33/0027* (2013.01); *G01S 17/00* (2013.01); *G01S 17/88* (2013.01); *G01S 17/89* (2013.01); *H01L 27/14601* (2013.01); *H04N 5/2256* (2013.01); *H04N 5/332* (2013.01); *G01N 2021/3155* (2013.01); *G01N 2201/0221* (2013.01); *G01N 2201/06113* (2013.01); *G06T 2207/10048* (2013.01)

(58) Field of Classification Search
USPC ...................................... 250/208.1, 221, 238
See application file for complete search history.

(56) References Cited

U.S. PATENT DOCUMENTS

| | | |
|---|---|---|
| 7,994,480 B2 | 8/2011 | Johnson et al. |
| 8,654,328 B2 | 2/2014 | Tkaczyk et al. |
| 8,760,509 B2 | 6/2014 | Schmidt et al. |
| 8,822,922 B1 | 9/2014 | Scanlon et al. |
| 9,464,984 B2 | 10/2016 | Schmidt et al. |
| 10,267,686 B2 * | 4/2019 | Kester .................. G01J 3/0256 |
| 2002/0071122 A1 | 6/2002 | Kulp et al. |
| 2009/0200466 A1 | 8/2009 | Mammen et al. |
| 2009/0231588 A1 | 9/2009 | Sutton et al. |
| 2013/0147951 A1 | 6/2013 | Brown et al. |
| 2013/0278771 A1 | 10/2013 | Magoun et al. |
| 2013/0321637 A1 | 12/2013 | Frank et al. |
| 2015/0269742 A1 | 9/2015 | Bergstrom et al. |
| 2015/0316473 A1 | 11/2015 | Kester et al. |
| 2015/0332441 A1 | 11/2015 | H?gasten et al. |
| 2015/0369730 A1 | 12/2015 | Schmidt et al. |
| 2016/0019428 A1 | 1/2016 | Vorbach |
| 2016/0080666 A1 | 3/2016 | Stuart et al. |
| 2016/0156880 A1 | 6/2016 | Teich et al. |
| 2016/0238451 A1 | 8/2016 | Zeng |
| 2017/0061663 A1 | 3/2017 | Johnson et al. |
| 2017/0272655 A1 | 9/2017 | Sakurai |
| 2018/0033704 A1 | 2/2018 | Suzuki et al. |
| 2018/0335380 A1 | 11/2018 | Schmidt et al. |

OTHER PUBLICATIONS

Thomas G. McRae and Thomas J. Kulp, Backscatter absorption gas imaging: a new technique for gas visualization, Jul. 20, 1993, 14 pages.

Uta-Barbara Goers, et al., Development of a compact gas imaging sensor employing a cw fiber-amp-pumped PPLN OPO, 2001, 1 page.

Thomas J. Kulp, et al., Development of a pulsed backscatter-absorption gas-imaging system and its application to the visualization of natural gas leaks, Jun. 20, 1998, 11 pages.

"Quantitative Optical Gas Imaging QL320 Training," Powerpoint Presentation by Providence Photonics, LLC presented Apr. 5, 2018 at 4C Conference in San Antonio, Texas, 120 pages.

Zeng et al., "Detection Limits for Optical Gas Imaging," Powerpoint Presentation by Providence Photonics, LLC, 4C conference in San Antonio, Texas, Apr. 3-5, 2018, 15 pages.

* cited by examiner

SYSTEMS AND METHODS FOR DETERMINING REGIONS SUITABLE FOR GAS IMAGING PROCESSES

CROSS-REFERENCES

This application is a continuation of U.S. application Ser. No. 15/284,146, filed Oct. 3, 2016, which is a continuation of U.S. application Ser. No. 14/310,914, filed Jun. 20, 2014, the content of both of these applications are incorporated herein by reference in their entirety.

BACKGROUND

Infrared imaging cameras are used in a variety of situations. For example, infrared imaging cameras are often used during maintenance inspections to thermally inspect equipment. Example equipment may include rotating machinery, electrical panels, or rows of circuit breakers, among other types of equipment. Infrared inspections can detect equipment hot spots such as overheating machinery or electrical components, helping to ensure timely repair or replacement of the overheating equipment before a more significant problem develops.

Depending on the configuration of the camera, the infrared imaging camera may also generate a visible light image of the same object. The camera may display the infrared image and the visible light image in a coordinated manner, for example, to help an operator interpret the thermal image generated by the thermal imaging camera.

Visible light and/or infrared imaging has been applied to the field of gas imaging, in which a user will inspect a target scene for the presence of a target gas. In a typical procedure, a user will illuminate the target scene with light of a wavelength that is absorbed by the target gas. In theory, the light incident on the target scene will either encounter the target gas and be at least partially absorbed, or will be scattered back to the camera at substantially full intensity from various portions of the target scene. Thus, if the camera detects substantially the full intensity of light of the illuminating wavelength from a portion of the target scene, such portion of the scene will be assumed to not comprise the target gas, as the light was not significantly absorbed. Conversely, illuminated portions of the target scene from which the camera does not detect or detects attenuated amounts of light of the illuminating wavelength are assumed to comprise the target gas, since the absence of backscattered light is indicative of the absorption properties of the gas.

These systems can be difficult to use effectively in the field due to varying background conditions that prevent or interfere with the backscattered illuminating light energy. For example, where no scattering background is present (e.g., sky in the background) there is no backscattered energy at all. In a similar manner, if the background is too far or angled away from the illuminating light source, the backscattered signal may be too weak to create a noticeable gas "shadow." This can be problematic because, where the backscatter is too weak, the weak or otherwise lack of gas shadow can cause a user to misinterpret the resulting image.

For example, if there is not an appropriate background for adequately scattering unabsorbed light toward the camera, the camera operator may falsely assume that the target gas is present in the target scene and is absorbing the illuminating light, since none of the light is scattered back toward the camera. On the other hand, in a setting in which backscatter is unlikely due to the background of the scene, a user may misinterpret a lack of detected backscattered light as an insufficient background as opposed to the target gas truly present in the target scene. In other examples, a background comprising angled or rounded surfaces can act to scatter light in directions away from the camera, resulting in a lack of backscattered energy incident on the camera in the absence of an absorbing target gas.

SUMMARY

Aspects of the present invention are directed towards methods and devices for performing illuminated gas imaging procedures. Embodiments include a method for detecting a target gas in a target scene. Embodiments of the method comprise capturing a first image of the target scene. The first image can be captured using a detector element sensitive over a range of wavelengths including a first wavelength that the target gas does not significantly absorb. The method can further include illuminating a first portion of the target scene with light of the first wavelength and capturing a second image of the target scene. Pixels of the first and second images can be compared, and based on the comparison, a gas detection image can be generated.

Generating a gas detection image can include, if the corresponding pixels in the first and second images are not sufficiently different, considering such a pixel to be an inoperable gas detection pixel. Conversely, if the corresponding pixels are sufficiently different, the pixel can be considered an operable gas detection pixel. The method can further include displaying the generated gas detection image. The gas detection image can be displayed such that inoperable gas detection pixels are presented in a distinguishing way from operable gas detection pixels. Thus, a user of the camera can observe the displayed gas detection image and visually determine which of the pixels in the target scene are operable gas detection pixels.

Exemplary methods can further include illuminating a second portion of the target scene with light of a second wavelength and capturing a third image of the target scene. The second wavelength can be an absorption wavelength of the target gas, wherein the target gas absorbs a significant amount of light of the second wavelength. The second portion of the target scene can at least partially overlap with the first portion. In some such embodiments, generating the gas detection image can comprise, for pixels considered to be operable gas detection pixels, including image data from the captured third image. Including image data from the third image can comprise determining a difference between image data in the third image and image data in at least one of the first or second images. The method can further include determining which of the operable gas detection pixels represent a portion of the target scene comprising the target gas.

Other aspects of the invention include a portable, handheld camera system. Embodiments of the system can include a light source capable of emitting light of a first wavelength that is not an absorption wavelength of a target gas, a camera module for detecting images of a target scene and a display for displaying at least a portion of an image. The system can include a processor and be configured to capture an image of the target scene, analyze a plurality of pixels in the image. In analyzing a plurality of pixels, the system can determine which of the analyzed pixels in the image are unsuitable for performing a gas imaging process of the target gas. The system can further alert a user of the presence of such unsuitable pixels. Alerting a user of such pixels can include, for example, displaying an image on the display in which pixels determined to be unsuitable for gas imaging are visually distinguishable from those not determined to be unsuitable. Embodiments of the system can include a second light source capable of emitting light of a second wavelength. The system can illuminate the target scene with light of the second wavelength and capture an image of the target scene illuminated with light of the second wavelength. Such an image can help the user visualize gas in the target scene, or allow the system to automatically detect gas in the target scene.

DETAILED DESCRIPTION

The following detailed description is exemplary in nature and is not intended to limit the scope, applicability, or configuration of the invention in any way. Rather, the following description provides some practical illustrations for implementing various embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

A thermal imaging camera may be used to detect heat patterns across a scene, including an object or objects, under observation. The thermal imaging camera may detect infrared radiation given off by the scene and convert the infrared radiation into an infrared image indicative of the heat patterns. In some embodiments, the thermal imaging camera may also capture visible light from the scene and convert the visible light into a visible light image. Depending on the configuration of the thermal imaging camera, the camera may include infrared optics to focus the infrared radiation on an infrared sensor and visible light optics to focus the visible light on a visible light sensor.

Figure 1:
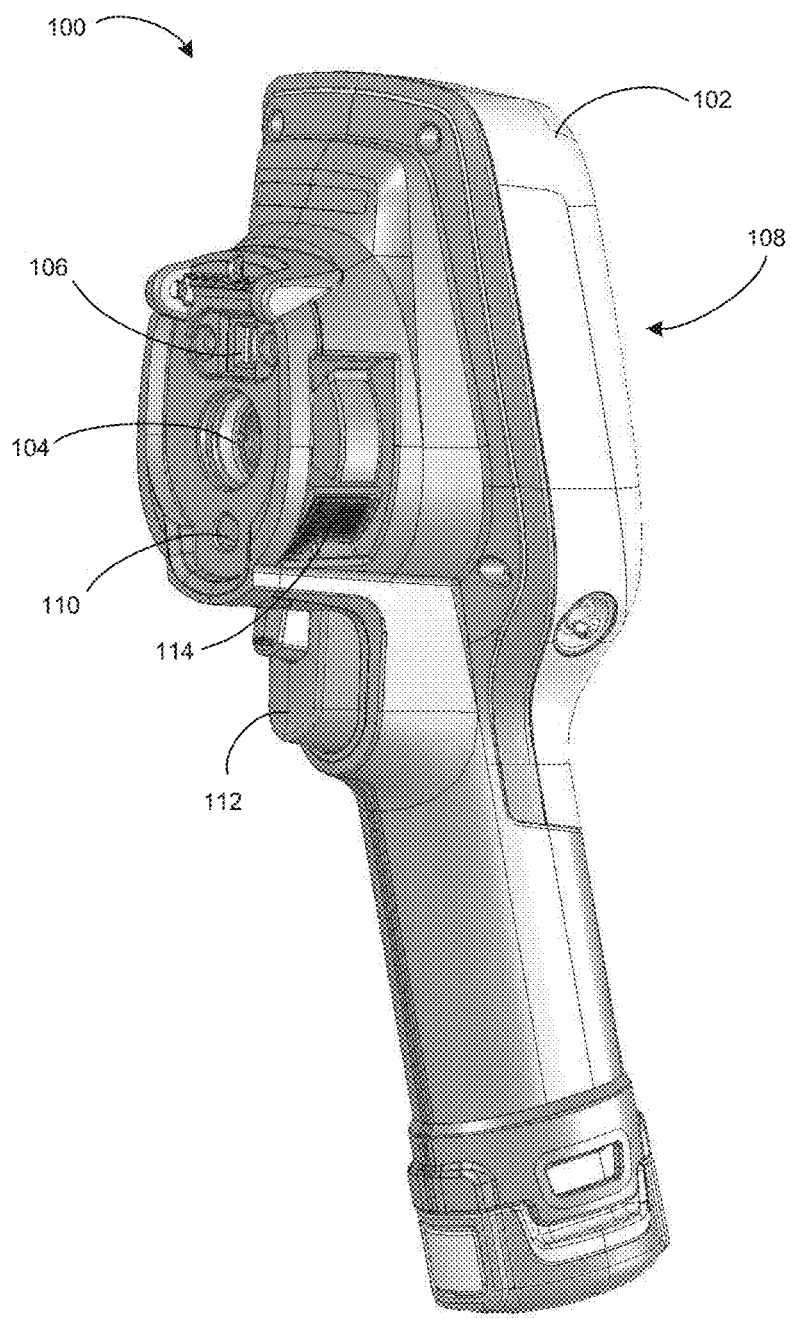
FIG. 1 is a perspective front view of an example thermal imaging camera.
Figure 2:
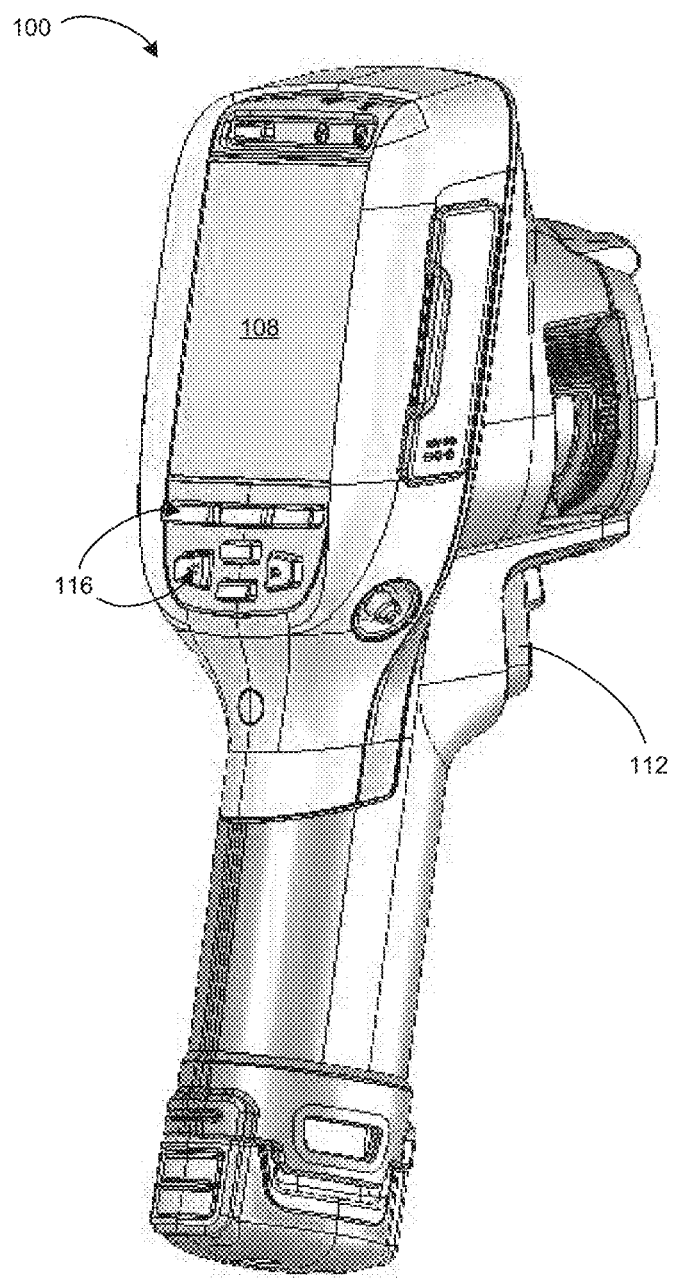
FIG. 2 is a perspective back view of the example thermal imaging camera of FIG. 1.

FIGS. 1 and 2 show front and back perspective views, respectively, of an example thermal imaging camera 100, which includes a housing 102, an infrared lens assembly 104, a visible light lens assembly 106, a display 108, a laser 110, and a trigger control 112. Housing 102 houses the various components of thermal imaging camera 100. The bottom portion of thermal imaging camera 100 includes a carrying handle for holding and operating the camera via one hand. Infrared lens assembly 104 receives infrared radiation from a scene and focuses the radiation on an infrared sensor for generating an infrared image of a scene. Visible light lens assembly 106 receives visible light from a scene and focuses the visible light on a visible light sensor for generating a visible light image of the same scene. Thermal imaging camera 100 captures the visible light image and/or the infrared image in response to depressing trigger control 112. In addition, thermal imaging camera 100 controls display 108 to display the infrared image and the visible light image generated by the camera, e.g., to help an operator thermally inspect a scene. Thermal imaging camera 100 may also include a focus mechanism coupled to infrared lens assembly 104 that is configured to move at least one lens of the infrared lens assembly so as to adjust the focus of an infrared image generated by the thermal imaging camera.

In operation, thermal imaging camera 100 detects heat patterns in a scene by receiving energy emitted in the infrared-wavelength spectrum from the scene and processing the infrared energy to generate a thermal image. Thermal imaging camera 100 may also generate a visible light image of the same scene by receiving energy in the visible light-wavelength spectrum and processing the visible light energy to generate a visible light image. As described in greater detail below, thermal imaging camera 100 may include an infrared camera module that is configured to capture an infrared image of the scene and a visible light camera module that is configured to capture a visible light image of the same scene. The infrared camera module may receive infrared radiation projected through infrared lens assembly 104 and generate therefrom infrared image data. The visible light camera module may receive light projected through visible light lens assembly 106 and generate therefrom visible light data.

In some examples, thermal imaging camera 100 collects or captures the infrared energy and visible light energy substantially simultaneously (e.g., at the same time) so that the visible light image and the infrared image generated by the camera are of the same scene at substantially the same time. In these examples, the infrared image generated by thermal imaging camera 100 is indicative of localized temperatures within the scene at a particular period of time while the visible light image generated by the camera is indicative of the same scene at the same period of time. In other examples, thermal imaging camera may capture infrared energy and visible light energy from a scene at different periods of time.

Visible light lens assembly 106 includes at least one lens that focuses visible light energy on a visible light sensor for generating a visible light image. Visible light lens assembly 106 defines a visible light optical axis which passes through the center of curvature of the at least one lens of the assembly. Visible light energy projects through a front of the lens and focuses on an opposite side of the lens. Visible light lens assembly 106 can include a single lens or a plurality of lenses (e.g., two, three, or more lenses) arranged in series. In addition, visible light lens assembly 106 can have a fixed focus or can include a focus adjustment mechanism for changing the focus of the visible light optics. In examples in which visible light lens assembly 106 includes a focus adjustment mechanism, the focus adjustment mechanism may be a manual adjustment mechanism or an automatic adjustment mechanism.

Infrared lens assembly 104 also includes at least one lens that focuses infrared energy on an infrared sensor for generating a thermal image. Infrared lens assembly 104 defines an infrared optical axis which passes through the center of curvature of lens of the assembly. During operation, infrared energy is directed through the front of the lens and focused on an opposite side of the lens. Infrared lens assembly 104 can include a single lens or a plurality of lenses (e.g., two, three, or more lenses), which may be arranged in series.

As briefly described above, thermal imaging camera 100 includes a focus mechanism for adjusting the focus of an infrared image captured by the camera. In the example shown in FIGS. 1 and 2, thermal imaging camera 100 includes focus ring 114. Focus ring 114 is operatively coupled (e.g., mechanically and/or electrically coupled) to at least one lens of infrared lens assembly 104 and configured to move the at least one lens to various focus positions so as to focus the infrared image captured by thermal imaging camera 100. Focus ring 114 may be manually rotated about at least a portion of housing 102 so as to move the at least one lens to which the focus ring is operatively coupled. In some examples, focus ring 114 is also operatively coupled to display 108 such that rotation of focus ring 114 causes at least a portion of a visible light image and at least a portion of an infrared image concurrently displayed on display 108 to move relative to one another. In different examples, thermal imaging camera 100 may include a manual focus adjustment mechanism that is implemented in a configuration other than focus ring 114, or may, in other embodiments, simply maintain a fixed focus.

In some examples, thermal imaging camera 100 may include an automatically adjusting focus mechanism in addition to or in lieu of a manually adjusting focus mechanism. An automatically adjusting focus mechanism may be operatively coupled to at least one lens of infrared lens assembly 104 and configured to automatically move the at least one lens to various focus positions, e.g., in response to instructions from thermal imaging camera 100. In one application of such an example, thermal imaging camera 100 may use laser 110 to electronically measure a distance between an object in a target scene and the camera, referred to as the distance-to-target. Thermal imaging camera 100 may then control the automatically adjusting focus mechanism to move the at least one lens of infrared lens assembly 104 to a focus position that corresponds to the distance-to-target data determined by thermal imaging camera 100. The focus position may correspond to the distance-to-target data in that the focus position may be configured to place the object in the target scene at the determined distance in focus. In some examples, the focus position set by the automatically adjusting focus mechanism may be manually overridden by an operator, e.g., by rotating focus ring 114.

Data of the distance-to-target, as measured by the laser 110, can be stored and associated with the corresponding captured image. For images which are captured using automatic focus, this data will be gathered as part of the focusing process. In some embodiments, the thermal imaging camera will also detect and save the distance-to-target data when an image is captured. This data may be obtained by the thermal imaging camera when the image is captured by using the laser 110 or, alternatively, by detecting the lens position and correlating the lens position to a known distance-to-target associated with that lens position. The distance-to-target data may be used by the thermal imaging camera 100 to direct the user to position the camera at the same distance from the target, such as by directing a user to move closer or further from the target based on laser measurements taken as the user repositions the camera, until the same distance-to-target is achieved as in an earlier image. The thermal imaging camera may further automatically set the lenses to the same positions as used in the earlier image, or may direct the user to reposition the lenses until the original lens settings are obtained.

During operation of thermal imaging camera 100, an operator may wish to view a thermal image of a scene and/or a visible light image of the same scene generated by the camera. For this reason, thermal imaging camera 100 may include a display. In the examples of FIGS. 1 and 2, thermal imaging camera 100 includes display 108, which is located on the back of housing 102 opposite infrared lens assembly 104 and visible light lens assembly 106. Display 108 may be configured to display a visible light image, an infrared image, and/or a combined image that includes a simultaneous display of the visible light image and the infrared image. In different examples, display 108 may be remote (e.g., separate) from infrared lens assembly 104 and visible light lens assembly 106 of thermal imaging camera 100, or display 108 may be in a different spatial arrangement relative to infrared lens assembly 104 and/or visible light lens assembly 106. Therefore, although display 108 is shown behind infrared lens assembly 104 and visible light lens assembly 106 in FIG. 2, other locations for display 108 are possible.

Thermal imaging camera 100 can include a variety of user input media for controlling the operation of the camera and adjusting different settings of the camera. Example control functions may include adjusting the focus of the infrared and/or visible light optics, opening/closing a shutter, capturing an infrared and/or visible light image, or the like. In the example of FIGS. 1 and 2, thermal imaging camera 100 includes a depressible trigger control 112 for capturing an infrared and visible light image, and buttons 116, which form part of the user interface, for controlling other aspects of the operation of the camera. A different number or arrangement of user input media are possible, and it should be appreciated that the disclosure is not limited in this respect. For example, thermal imaging camera 100 may include a touch screen display 108 which receives user input by depressing different portions of the screen.

Figure 3:
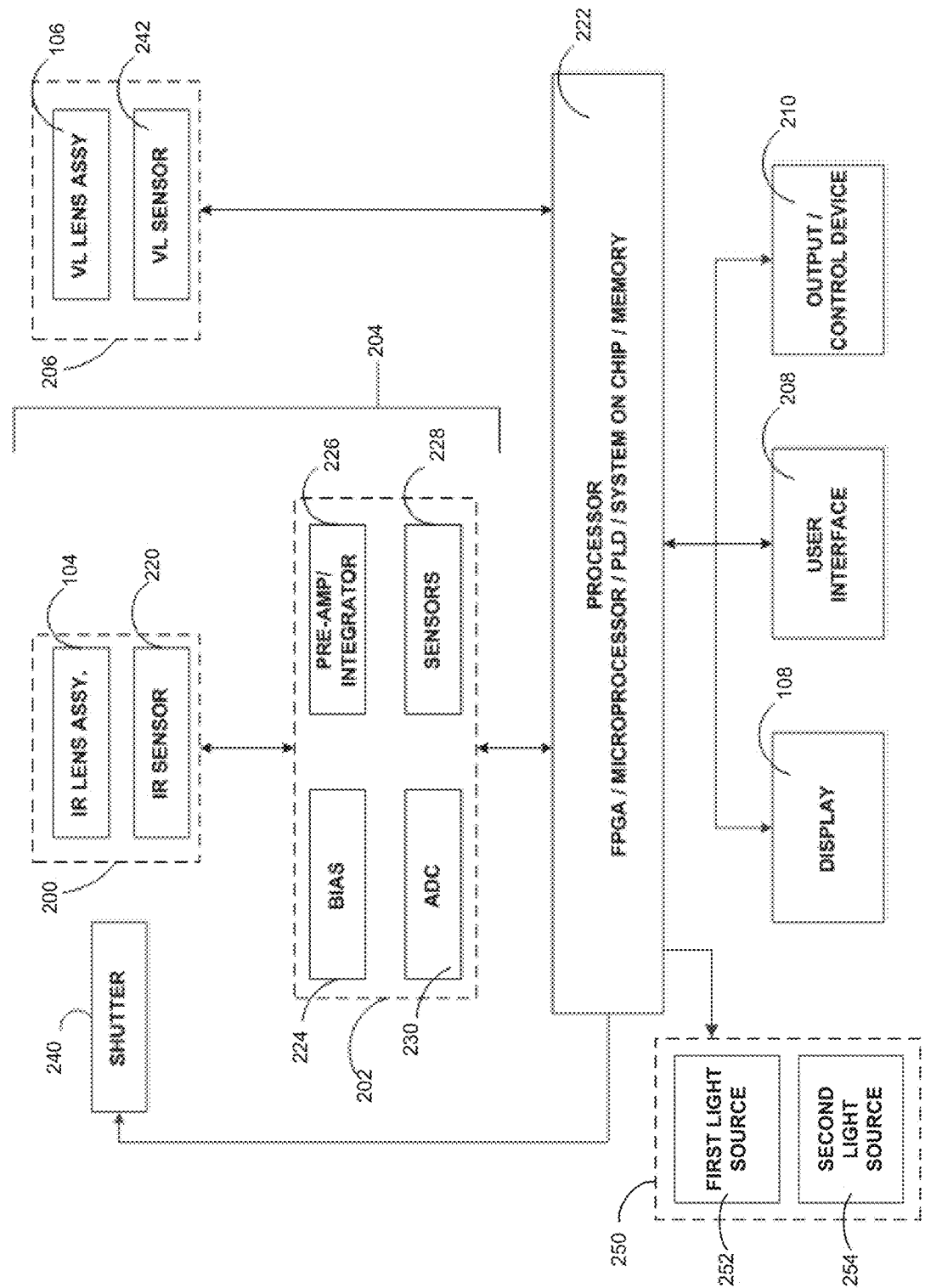
FIG. 3 is a functional block diagram illustrating example components of the thermal imaging camera of FIGS. 1 and 2.

FIG. 3 is a functional block diagram illustrating components of an example of thermal imaging camera 100. Thermal imaging camera 100 includes an IR camera module 200, front end circuitry 202. The IR camera module 200 and front end circuitry 202 are sometimes referred to in combination as front end stage or front end components 204 of the infrared camera 100. Thermal imaging camera 100 may also include a visible light camera module 206, a display 108, a user interface 208, and an output/control device 210.

Infrared camera module 200 may be configured to receive infrared energy emitted by a target scene and to focus the infrared energy on an infrared sensor for generation of infrared energy data, e.g., that can be displayed in the form of an infrared image on display 108 and/or stored in memory. Infrared camera module 200 can include any suitable components for performing the functions attributed to the module herein. In the example of FIG. 3, infrared camera module 200 is illustrated as including infrared lens assembly 104 and infrared sensor 220. As described above with respect to FIGS. 1 and 2, infrared lens assembly 104 includes at least one lens that takes infrared energy emitted by a target scene and focuses the infrared energy on infrared sensor 220. Infrared sensor 220 responds to the focused infrared energy by generating an electrical signal that can be converted and displayed as an infrared image on display 108.

Infrared sensor 220 may include one or more focal plane arrays (FPA) that generate electrical signals in response to infrared energy received through infrared lens assembly 104. Each FPA can include a plurality of infrared sensor elements including, e.g., bolometers, photon detectors, or other suitable infrared sensor elements. In operation, each sensor element, which may each be referred to as a sensor pixel, may change an electrical characteristic (e.g., voltage or resistance) in response to absorbing infrared energy received from a target scene. In turn, the change in electrical characteristic can provide an electrical signal that can be received by a processor 222 and processed into an infrared image displayed on display 108.

For instance, in examples in which infrared sensor 220 includes a plurality of bolometers, each bolometer may absorb infrared energy focused through infrared lens assembly 104 and increase in temperature in response to the absorbed energy. The electrical resistance of each bolometer may change as the temperature of the bolometer changes. With each detector element functioning as a sensor pixel, a two-dimensional image or picture representation of the infrared radiation can be further generated by translating the changes in resistance of each detector element into a time-multiplexed electrical signal that can be processed for visualization on a display or storage in memory (e.g., of a computer). Processor 222 may measure the change in resistance of each bolometer by applying a current (or voltage) to each bolometer and measure the resulting voltage (or current) across the bolometer. Based on these data, processor 222 can determine the amount of infrared energy emitted by different portions of a target scene and control display 108 to display a thermal image of the target scene.

Independent of the specific type of infrared sensor elements included in the FPA of infrared sensor 220, the FPA array can define any suitable size and shape. In some examples, infrared sensor 220 includes a plurality of infrared sensor elements arranged in a grid pattern such as, e.g., an array of sensor elements arranged in vertical columns and horizontal rows. In various examples, infrared sensor 220 may include an array of vertical columns by horizontal rows of, e.g., 16×16, 50×50, 160×120, 120×160, or 650×480. In other examples, infrared sensor 220 may include a smaller number of vertical columns and horizontal rows (e.g., 1×1), a larger number vertical columns and horizontal rows (e.g., 1000×1000), or a different ratio of columns to rows.

In certain embodiments a Read Out Integrated Circuit (ROIC) is incorporated on the IR sensor 220. The ROIC is used to output signals corresponding to each of the sensor pixels. Such ROIC is commonly fabricated as an integrated circuit on a silicon substrate. The plurality of detector elements may be fabricated on top of the ROIC, wherein their combination provides for the IR sensor 220. In some embodiments, the ROIC can include components discussed elsewhere in this disclosure (e.g. an analog-to-digital converter (ADC)) incorporated directly onto the FPA circuitry. Such integration of the ROIC, or other further levels of integration not explicitly discussed, should be considered within the scope of this disclosure.

As described above, the IR sensor 220 generates a series of electrical signals corresponding to the infrared radiation received by each infrared detector element to represent a thermal image. A "frame" of thermal image data is generated when the voltage signal from each infrared detector element is obtained by scanning all of the rows that make up the IR sensor 220. Again, in certain embodiments involving bolometers as the infrared detector elements, such scanning is done by switching a corresponding detector element into the system circuit and applying a bias voltage across such switched-in element. Successive frames of thermal image data are generated by repeatedly scanning the rows of the IR sensor 220, with such frames being produced at a rate sufficient to generate a video representation (e.g. 30 Hz, or 60 Hz) of the thermal image data.

The front end circuitry 202 includes circuitry for interfacing with and controlling the IR camera module 200. In addition, the front end circuitry 202 initially processes and transmits collected infrared image data to a processor 222 via a connection therebetween. More specifically, the signals generated by the IR sensor 220 are initially conditioned by the front end circuitry 202 of the thermal imaging camera 100. In certain embodiments, as shown, the front end circuitry 202 includes a bias generator 224 and a pre-amp/integrator 226. In addition to providing the detector bias, the bias generator 224 can optionally add or subtract an average bias current from the total current generated for each switched-in detector element. The average bias current can be changed in order (i) to compensate for deviations to the entire array of resistances of the detector elements resulting from changes in ambient temperatures inside the thermal imaging camera 100 and (ii) to compensate for array-to-array variations in the average detector elements of the IR sensor 220. Such bias compensation can be automatically controlled by the thermal imaging camera 100 or software, or can be user controlled via input to the output/control device 210 or processor 222. Following provision of the detector bias and optional subtraction or addition of the average bias current, the signals can be passed through a pre-amp/integrator 226. Typically, the pre-amp/integrator 226 is used to condition incoming signals, e.g., prior to their digitization. As a result, the incoming signals can be adjusted to a form that enables more effective interpretation of the signals, and in turn, can lead to more effective resolution of the created image. Subsequently, the conditioned signals are sent downstream into the processor 222 of the thermal imaging camera 100.

In some embodiments, the front end circuitry 202 can include one or more additional elements for example, additional sensors 228 or an ADC 230. Additional sensors 228 can include, for example, temperature sensors, visual light sensors (such as a CCD), pressure sensors, magnetic sensors, etc. Such sensors can provide additional calibration and detection information to enhance the functionality of the thermal imaging camera 100. For example, temperature sensors can provide an ambient temperature reading near the IR sensor 220 to assist in radiometry calculations. A magnetic sensor, such as a Hall effect sensor, can be used in combination with a magnet mounted on the lens to provide lens focus position information. Such information can be useful for calculating distances, or determining a parallax offset for use with visual light scene data gathered from a visual light sensor.

An ADC 230 can provide the same function and operate in substantially the same manner as discussed below, however its inclusion in the front end circuitry 202 may provide certain benefits, for example, digitization of scene and other sensor information prior to transmittal to the processor 222 via the connection therebetween. In some embodiments, the ADC 230 can be integrated into the ROIC, as discussed above, thereby eliminating the need for a separately mounted and installed ADC 230.

In some embodiments, front end components can further include a shutter 240. A shutter 240 can be externally or internally located relative to the lens and operate to open or close the view provided by the IR lens assembly 104. As is known in the art, the shutter 240 can be mechanically positionable, or can be actuated by an electro-mechanical device such as a DC motor or solenoid. Embodiments of the invention may include a calibration or setup software implemented method or setting which utilize the shutter 240 to establish appropriate bias levels for each detector element.

Components described as processors within thermal imaging camera 100, including processor 222, may be implemented as one or more processors, such as one or more microprocessors, digital signal processors (DSPs), application specific integrated circuits (ASICs), field programmable gate arrays (FPGAs), programmable logic circuitry, or the like, either alone or in any suitable combination. Processor 222 may also include memory that stores program instructions and related data that, when executed by processor 222, cause thermal imaging camera 100 and processor 222 to perform the functions attributed to them in this disclosure. Memory may include any fixed or removable magnetic, optical, or electrical media, such as RAM, ROM, CD-ROM, hard or floppy magnetic disks, EEPROM, or the like. Memory may also include a removable memory portion that may be used to provide memory updates or increases in memory capacities. A removable memory may also allow image data to be easily transferred to another computing device, or to be removed before thermal imaging camera 100 is used in another application. Processor 222 may also be implemented as a System on Chip that integrates all components of a computer or other electronic system into a single chip. These elements manipulate the conditioned scene image data delivered from the front end stages 204 in order to provide output scene data that can be displayed or stored for use by the user. Subsequently, the processor 222 (processing circuitry) sends the processed data to a display 108 or other output/control device 210.

During operation of thermal imaging camera 100, processor 222 can control infrared camera module 200 to generate infrared image data for creating an infrared image. Processor 222 can generate a digital "frame" of infrared image data. By generating a frame of infrared image data, processor 222 captures an infrared image of a target scene at a given point in time.

Processor 222 can capture a single infrared image or "snap shot" of a target scene by measuring the electrical signal of each infrared sensor element included in the FPA of infrared sensor 220 a single time. Alternatively, processor 222 can capture a plurality of infrared images of a target scene by repeatedly measuring the electrical signal of each infrared sensor element included in the FPA of infrared sensor 220. In examples in which processor 222 repeatedly measures the electrical signal of each infrared sensor element included in the FPA of infrared sensor 220, processor 222 may generate a dynamic thermal image (e.g., a video representation) of a target scene. For example, processor 222 may measure the electrical signal of each infrared sensor element included in the FPA at a rate sufficient to generate a video representation of thermal image data such as, e.g., 30 Hz or 60 Hz. Processor 222 may perform other operations in capturing an infrared image such as sequentially actuating a shutter 240 to open and close an aperture of infrared lens assembly 104, or the like.

With each sensor element of infrared sensor 220 functioning as a sensor pixel, processor 222 can generate a two-dimensional image or picture representation of the infrared radiation from a target scene by translating changes in an electrical characteristic (e.g., resistance) of each sensor element into a time-multiplexed electrical signal that can be processed, e.g., for visualization on display 108 and/or storage in memory. When displayed on a display 108, an infrared image can comprise a plurality of display pixels. Display pixels can have any defined relationship with corresponding sensor pixels. In some examples, each sensor pixel corresponds to a display pixel in an image representation of infrared data. In other examples, a plurality of sensor pixels may be combined (e.g., averaged) to provide infrared information for a single display pixel. Because relationships between display pixels and sensor pixels are defined with respect to camera operation, the generic term "pixel" may refer to the sensor pixel, the display pixel, or the data as it is processed from the sensor pixel to the display pixel unless otherwise stated. Processor 222 may perform computations to convert raw infrared image data into scene temperatures (radiometry) including, in some examples, colors corresponding to the scene temperatures.

Processor 222 may control display 108 to display at least a portion of an infrared image of a captured target scene. In some examples, processor 222 controls display 108 so that the electrical response of each sensor element of infrared sensor 220 is associated with a single pixel on display 108. In other examples, processor 222 may increase or decrease the resolution of an infrared image so that there are more or fewer pixels displayed on display 108 than there are sensor elements in infrared sensor 220. Processor 222 may control display 108 to display an entire infrared image (e.g., all portions of a target scene captured by thermal imaging camera 100) or less than an entire infrared image (e.g., a lesser port of the entire target scene captured by thermal imaging camera 100). Processor 222 may perform other image processing functions, as described in greater detail below.

Independent of the specific circuitry, thermal imaging camera 100 may be configured to manipulate data representative of a target scene so as to provide an output that can be displayed, stored, transmitted, or otherwise utilized by a user.

Thermal imaging camera 100 includes visible light camera module 206. Visible light camera module 206 may be configured to receive visible light energy from a target scene and to focus the visible light energy on a visible light sensor for generation of visible light energy data, e.g., that can be displayed in the form of a visible light image on display 108 and/or stored in memory. Visible light camera module 206 can include any suitable components for performing the functions attributed to the module herein. In the example of FIG. 3, visible light camera module 206 is illustrated as including visible light lens assembly 106 and visible light sensor 242. As described above with respect to FIGS. 1 and 2, visible light lens assembly 106 includes at least one lens that takes visible light energy emitted by a target scene and focuses the visible light energy on visible light sensor 242. Visible light sensor 242 responds to the focused energy by generating an electrical signal that can be converted and displayed as a visible light image on display 108.

Visible light sensor 242 may include a plurality of visible light sensor elements such as, e.g., CMOS detectors, CCD detectors, PIN diodes, avalanche photo diodes, or the like. The number of visible light sensor elements may be the same as or different than the number of infrared light sensor elements.

In operation, optical energy received from a target scene may pass through visible light lens assembly 106 and be focused on visible light sensor 242. When the optical energy impinges upon the visible light sensor elements of visible light sensor 242, photons within the photodetectors may be released and converted into a detection current. Processor 222 can process this detection current to form a visible light image of the target scene.

During use of thermal imaging camera 100, processor 222 can control visible light camera module 206 to generate visible light data from a captured target scene for creating a visible light image. The visible light data may include luminosity data indicative of the color(s) associated with different portions of the captured target scene and/or the magnitude of light associated with different portions of the captured target scene. Processor 222 can generate a "frame" of visible light image data by measuring the response of each visible light sensor element of thermal imaging camera 100 a single time. By generating a frame of visible light data, processor 222 captures visible light image of a target scene at a given point in time. Processor 222 may also repeatedly measure the response of each visible light sensor element of thermal imaging camera 100 so as to generate a dynamic thermal image (e.g., a video representation) of a target scene, as described above with respect to infrared camera module 200.

With each sensor element of visible light camera module 206 functioning as a sensor pixel, processor 222 can generate a two-dimensional image or picture representation of the visible light from a target scene by translating an electrical response of each sensor element into a time-multiplexed electrical signal that can be processed, e.g., for visualization on display 108 and/or storage in memory.

Processor 222 may control display 108 to display at least a portion of a visible light image of a captured target scene. In some examples, processor 222 controls display 108 so that the electrical response of each sensor element of visible light camera module 206 is associated with a single pixel on display 108. In other examples, processor 222 may increase or decrease the resolution of a visible light image so that there are more or fewer pixels displayed on display 108 than there are sensor elements in visible light camera module 206. Processor 222 may control display 108 to display an entire visible light image (e.g., all portions of a target scene captured by thermal imaging camera 100) or less than an entire visible light image (e.g., a lesser port of the entire target scene captured by thermal imaging camera 100).

As noted above, processor 222 may be configured to determine a distance between thermal imaging camera 100 and an object in a target scene captured by a visible light image and/or infrared image generated by the camera. Processor 222 may determine the distance based on a focus position of the infrared optics associated with the camera. For example, processor 222 may detect a position (e.g., a physical position) of a focus mechanism associated with the infrared optics of the camera (e.g., a focus position associated with the infrared optics) and determine a distance-to-target value associated with the position. Processor 222 may then reference data stored in memory that associates different positions with different distance-to-target values to determine a specific distance between thermal imaging camera 100 and the object in the target scene.

In these and other examples, processor 222 may control display 108 to concurrently display at least a portion of the visible light image captured by thermal imaging camera 100 and at least a portion of the infrared image captured by thermal imaging camera 100. Such a concurrent display may be useful in that an operator may reference the features displayed in the visible light image to help understand the features concurrently displayed in the infrared image, as the operator may more easily recognize and distinguish different real-world features in the visible light image than the infrared image. In various examples, processor 222 may control display 108 to display the visible light image and the infrared image in side-by-side arrangement, in a picture-in-picture arrangement, where one of the images surrounds the other of the images, or any other suitable arrangement where the visible light and the infrared image are concurrently displayed.

For example, processor 222 may control display 108 to display the visible light image and the infrared image in a combined arrangement. In such an arrangement, for a pixel or set of pixels in the visible light image representative of a portion of the target scene, there exists a corresponding pixel or set of pixels in the infrared image, representative of substantially the same portion of the target scene. Thus, in some such arrangements, the visible light image and the infrared image may be superimposed on top of one another, at corresponding pixels. In general, "corresponding pixels" in any plurality of images or sets of image data can be used to describe pixels in the respective images or sets of image data representative of substantially the same portions of a target scene.

An operator may interact with user interface 208 to control the transparency or opaqueness of one or both of the images displayed on display 108. For example, the operator may interact with user interface 208 to adjust the infrared image between being completely transparent and completely opaque and also adjust the visible light image between being completely transparent and completely opaque. Such an exemplary combined arrangement, which may be referred to as an alpha-blended arrangement, may allow an operator to adjust display 108 to display an infrared-only image, a visible light-only image, of any overlapping combination of the two images between the extremes of an infrared-only image and a visible light-only image. Processor 222 may also combine scene information with other data, such as radiometric data, alarm data, and the like. In general, an alpha-blended combination of visible light and infrared images can comprise anywhere from 100 percent infrared and 0 percent visible light to 0 percent infrared and 100 percent visible light. In some embodiments, the amount of blending can be adjusted by a user of the camera. Thus, in some embodiments, a blended image can be adjusted between 100 percent visible light and 100 percent infrared.

Additionally, in some embodiments, the processor 222 can interpret and execute commands from user interface 208, an output/control device 210. This can involve processing of various input signals and transferring those signals to the front end circuitry 202 via a connection therebetween. Components (e.g. motors, or solenoids) proximate the front end circuitry 202 can be actuated to accomplish the desired control function. Exemplary control functions can include adjusting the focus, opening/closing a shutter, triggering sensor readings, adjusting bias values, etc. Moreover, input signals may be used to alter the processing of the image data that occurs in the processor 222.

Processor can further include other components to assist with the processing and control of the infrared imaging camera 100. For example, as discussed above, in some embodiments, an ADC can be incorporated into the processor 222. In such a case, analog signals conditioned by the front-end stages 204 are not digitized until reaching the processor 222. Moreover, some embodiments can include additional on board memory for storage of processing command information and scene data, prior to transmission to the display 108 or the output/control device 210.

An operator may interact with thermal imaging camera 100 via user interface 208, which may include buttons, keys, or another mechanism for receiving input from a user. The operator may receive output from thermal imaging camera 100 via display 108. Display 108 may be configured to display an infrared-image and/or a visible light image in any acceptable palette, or color scheme, and the palette may vary, e.g., in response to user control. In some examples, display 108 is configured to display an infrared image in a monochromatic palette such as grayscale or amber. In other examples, display 108 is configured to display an infrared image in a color palette such as, e.g., ironbow, blue-red, or other high contrast color scheme. Combinations of grayscale and color palette displays are also contemplated.

While processor 222 can control display 108 to concurrently display at least a portion of an infrared image and at least a portion of a visible light image in any suitable arrangement, a picture-in-picture arrangement may help an operator to easily focus and/or interpret a thermal image by displaying a corresponding visible image of the same scene in adjacent alignment.

A power supply (not shown) delivers operating power to the various components of thermal imaging camera 100 and, in some examples, may include a rechargeable or non-rechargeable battery and a power generation circuit.

During operation of thermal imaging camera 100, processor 222 controls infrared camera module 200 and visible light camera module 206 with the aid of instructions associated with program information that is stored in memory to generate a visible light image and an infrared image of a target scene. Processor 222 further controls display 108 to display the visible light image and/or the infrared image generated by thermal imaging camera 100.

In some embodiments, a camera can include a light source for emitting light at one or more wavelengths toward a target scene. The camera can include a single light source configured to emit light at a plurality of wavelengths, or can include a plurality of light sources for emitting a plurality of wavelengths of light. In some embodiments, the camera can be part of a system including a light source array or light source module comprising one or more light sources. As shown in FIG. 3, an exemplary light source array 250 comprising a first light source 252 and a second light source 254 is shown as being in communication with the camera processor 222. First 252 and second 254 light sources can be configured to emit light at first and second wavelengths, respectively. In various embodiments, the light source array 250 can be integral to or separable from the camera.

The one or more light sources of the light source array can be any appropriate source for emitting desired wavelengths of light. Exemplary light sources can include lasers such as quantum cascade lasers (QCL's) other laser types (e.g., gas, fiber, crystal, semiconductor, etc.), diodes such as light emitting diodes (LED's), and the like. In some examples, light sources can be tunable, wherein the wavelength of light is adjustable. QCL's, for example, have an adjustable wavelength. The light source array can include a broadband emitter, such as an incandescent bulb. Broadband emissions can be manipulated to extract a desired wavelength therefrom by filters, gratings, prisms, or other appropriate optical devices. It will be appreciated that any number of light sources are possible for emitting desired wavelengths of light toward a target scene.

The light source array can further include a set of optics to direct and shape the light emitted from the light source array 250 in a desired manner. For example, in some configurations, one or more lenses are disposed in the path of a laser such that the one or more lenses outputs a diverging cone of light at the predetermined wavelength. In other embodiments, the emitted light can be collimated and directed toward the target scene. In still further embodiments, the light source array can be configured to raster light from the light source across an area of the target scene, effectively illuminating an area over a period of time. Light sources and optics can be selected based on available space or power available, for example. In some configurations, a camera includes a battery or other power source that can provide electrical power to the one or more light sources.

As discussed elsewhere herein, cameras can be used for the detection of a target gas present in the target scene. In particular, the absorption properties of the target gas about an absorption wavelength can allow for detection/imaging of the target gas. Accordingly, in some embodiments, at least one light source in the light source array 250 is configured to emit light at a wavelength that is an absorption wavelength of the target gas. That is, the at least one light source is configured to emit light of a wavelength that is significantly absorbed by the target gas. It will be appreciated that significant absorption of light does not necessarily imply that the target gas absorbs 100% of the light at that wavelength. Rather, the target gas absorbs a measureable, observable, or otherwise significant and detectable amount of light at the absorption wavelength. Similarly, a wavelength that is not an absorbing wavelength may be absorbed some negligible or otherwise small amount by a target gas.

A second light source can emit light at a wavelength that is approximately the same as the absorption wavelength, but is not substantially absorbed by the target gas. That is, the target gas may absorb a small or negligible amount of light at that wavelength. In an exemplary embodiment, the first light source 252 emits light at a first wavelength while the second light source 254 emits light at a second wavelength, the second wavelength being an absorption wavelength of the target gas and the first wavelength being approximately, but not equal to, the second wavelength, such that the first wavelength is not significantly absorbed by the target gas. In some embodiments, a camera can include a sensor for detecting images of a target scene that is sensitive to a range of wavelengths including the first and second wavelengths.

During general gas imaging operation, a user can utilize a camera to assist in the detection of a target gas. As described elsewhere herein, to detect a target gas in a target scene, a user can emit light at an absorption wavelength of the gas toward the target scene. If the light encounters the gas, a significant portion of the light it will be absorbed, whereas if gas is not encountered, the gas will be scattered by an element in the target scene. This is illustrated by the broken lines representing the propagation of such light in FIG. 4A. As shown, light of an absorption wavelength is emitted toward a target scene. Some light encounters the target gas 260 and is absorbed, while remaining light scatters back from the target scene off background 262. However, in some instances, such as is depicted in FIG. 4B, there is not a sufficient background off which such light can scatter.

Figure 4A:
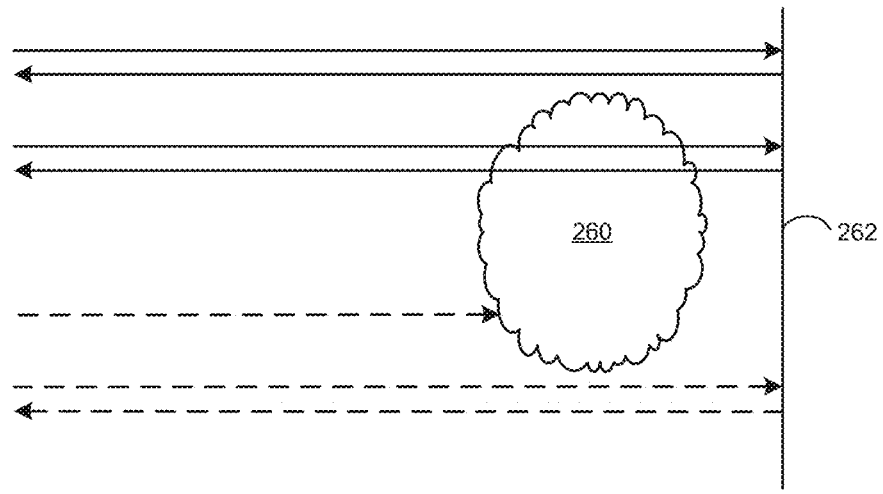
FIGS. 4A and 4B are exemplary schematic diagrams of traditional gas imaging techniques.
Figure 4B:
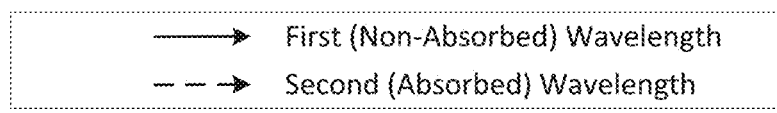
Figure 4B:
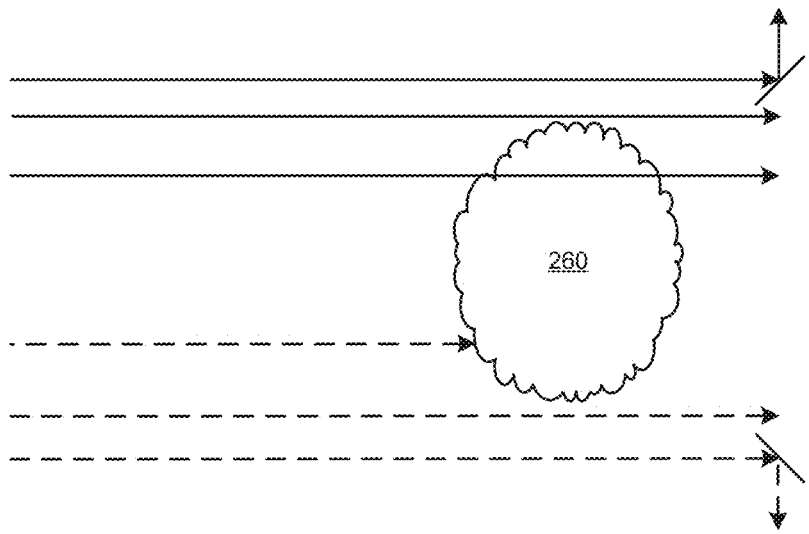

As shown in FIG. 4B, light of an absorption wavelength of the target gas (represented by a broken line) is either absorbed by the gas 260 or propagates beyond the gas, encountering no background off which to scatter. Accordingly, a camera configured to detect the presence of gas based on unabsorbed, scattered light will be unable to detect any scattered light, and will therefore be prone to inaccurate gas detection operation. Similarly, in some situations the light can encounter a background that is rounded or otherwise angled so as to not scatter a significant amount of light back toward the camera. Embodiments of the invention can be utilized to alert the user of an inability to adequately perform a gas imaging or detection operation because of a lack of appropriate background.

In accordance with some embodiments of the invention, a user can emit light at a first wavelength which is not significantly absorbed by the target gas toward the target scene via a first light source. As illustrated in FIG. 4A, light of the first wavelength (shown in solid lines) is directed toward a target scene having background 262. Because the first wavelength is not significantly absorbed by the target gas, the light is scattered off of background 262 back toward the camera regardless of whether or not the light encounters the gas 260. Accordingly, if light of the first wavelength is not detected (such as in the situation of FIG. 4B), it is likely that it was not sufficiently scattered back toward the camera. Thus, by imaging the target scene while emitting light of the first, substantially non-absorption wavelength, it can become possible to determine where in the target scene there exists an adequate background for performing gas imaging with an absorption wavelength of the target gas.

In general, any gas that absorbs light of a certain wavelength can be detected with an appropriate imaging device and light source. In some embodiments of the invention, the first (non-absorbing) wavelength used in conjunction with a second (absorbing) wavelength in a gas imaging operation is substantially close in value to the second wavelength while still not being significantly absorbed by the gas. This can be done to minimize the wavelength-dependent differences in the propagation and/or imaging of light of the two wavelengths. The degree to which the first and second wavelengths are substantially close in value can vary depending on the target gas and its absorption spectrum. In some examples, the first and second wavelengths can be within approximately 50 nm of one another. However, if the absorption spectrum of the target gas is relatively wide, the first and second wavelengths can be further apart. If the spectrum is narrower, the first and second wavelengths can be closer together. In some embodiments, the first and second wavelengths can be determined based on a user selected target gas.

Figure 5:
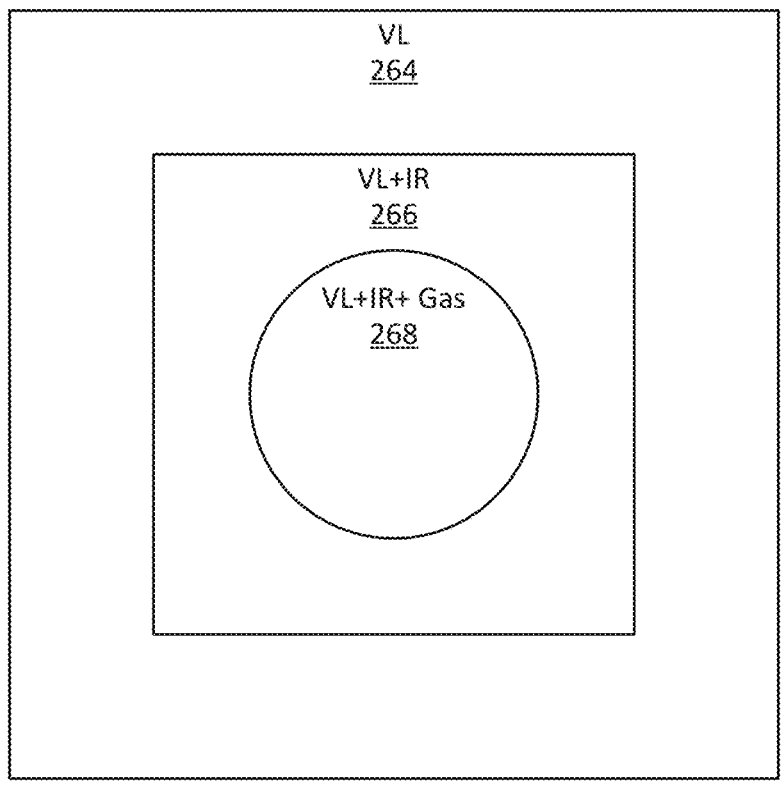
FIG. 5 illustrates an exemplary gas detection image that can be produced by an infrared camera according to some embodiments of the invention.

In some examples, a camera is configured to detect gas such as methane or other hydrocarbons. Such gases often include absorption wavelengths in the infrared range. Accordingly, thermal imagers comprising infrared detector elements such as described above can be used for performing such gas imaging operations. Similarly, first 252 and second 254 light sources can be configured to emit light in the infrared spectrum. In such embodiments, aspects and methods of infrared and/or combined infrared and visible light imaging can be applied. For example, FIG. 5 illustrates an exemplary gas detection image that can be produced by an infrared camera according to some embodiments. The illustrated example comprises a picture-in-picture arrangement, in which a portion of the image 266 comprising visible light and infrared image data appears within an area 264 that comprises entirely visible light image data. In addition, a portion 268 of the combined visible light and infrared area of the image can also be used to present gas detection information of the target scene.

It should be appreciated that, while many examples described herein will include infrared light sources and detectors, the scope of the invention need not be limited to such embodiments. More generally, embodiments of the invention can be applied to gases with absorption wavelengths in any spectrum, such as visible light or ultraviolet. Such embodiments can include first and second light sources in the spectrum of the absorption wavelengths, as well as a detector sensitive to a spectrum of light including the first and second wavelengths. In some embodiments, a user can select wavelengths of light to be emitted from a light source array to perform gas imaging processes based upon a particular target gas.

Figure 6:
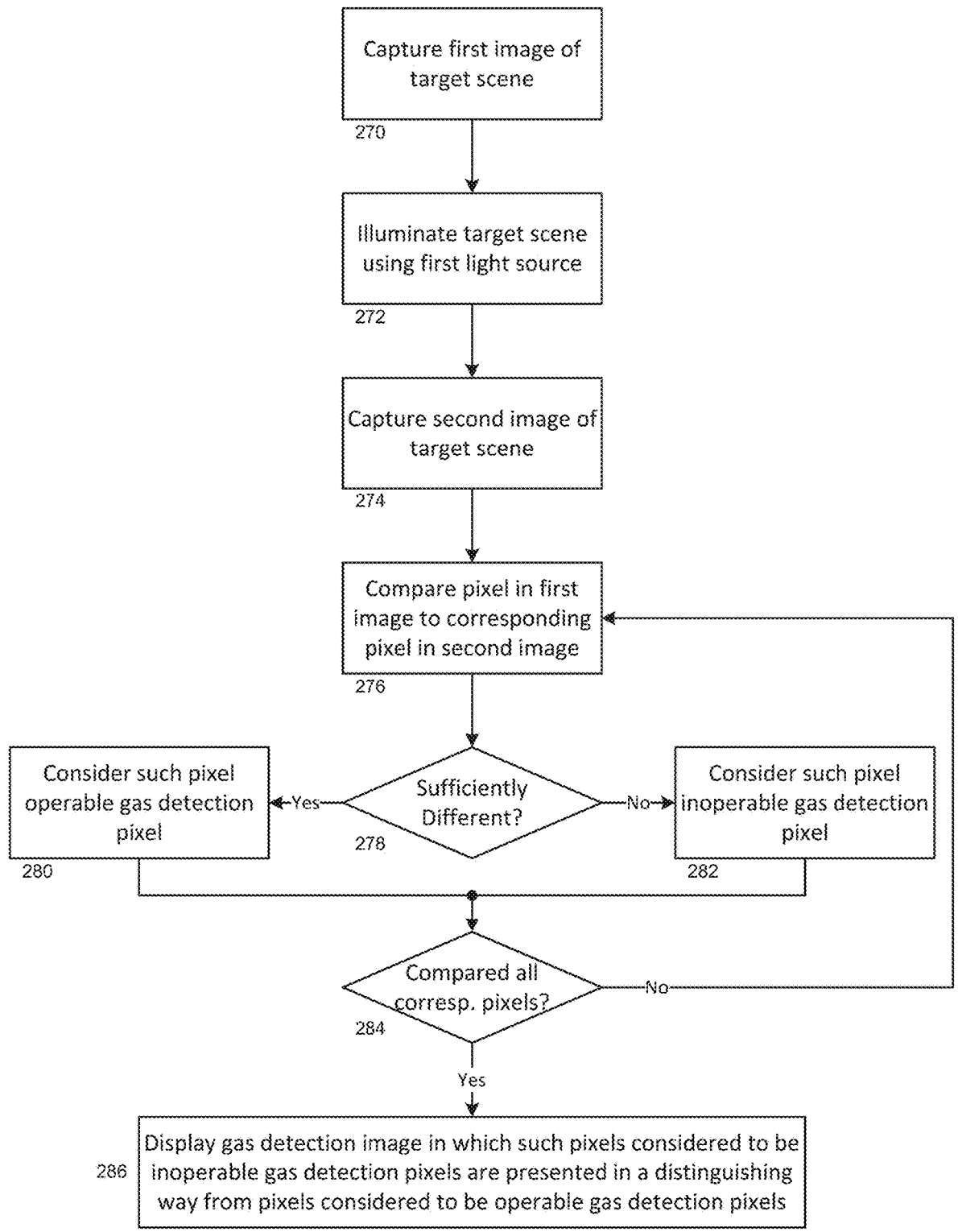
FIG. 6 is a process flow diagram illustrating a method for determining which parts of a target scene include an adequate background for detecting a target gas in the target scene.

FIG. 6 is a process flow diagram illustrating a method for determining which parts of a target scene include an adequate background for detecting a target gas in the target scene. First a camera can be used to capture 270 a first image of a target scene. Next, the camera can be used to illuminate 272 the target scene using a first light source. The first light source can be configured to emit light at a first wavelength such that the first wavelength can be detected by the camera but is not significantly absorbed by the target gas as previously discussed. In some examples, the first wavelength is an infrared wavelength. The camera can then be used to capture 274 a second image of the target scene while it is illuminated via the first light source.

The camera, for example via processor 222, can act to compare 276 pixels in the first image to corresponding pixels in the second image. In some embodiments, the camera compares corresponding pixels that make up a subset of the captured image. In some examples, the compared subset of pixels can include only pixels whose target area intersects with the light emitted from the light source at the imaging place. That is, pixels that are not likely to detect scattered light from the light source need not be analyzed for receiving the scattered light.

In comparing 276 corresponding pixels, the camera can determine 278 if the corresponding pixels between the first and second images are sufficiently different. Determining a sufficient difference between corresponding pixels can include comparing the difference between the pixels to a threshold, wherein if the difference exceeds the threshold, the pixels are sufficiently different. In various embodiments, the threshold can be fixed, wherein the same threshold is used in all imaging operations, or can be gas and/or wavelength dependent. In some examples, the threshold can be determined from the absorption spectrum of the target gas. Because the light is not significantly absorbed by the target gas, a sufficient difference between the first and second images suggests that emitted light of the first wavelength is sufficiently scattered back to the detector. Thus, the target scene represented in such pixel comprises a background such as 262 in FIG. 4A which effectively scatters light back to the camera. In such a case, the camera can consider 280 such a pixel to be an operable gas detection pixel. However, if the corresponding pixels are not sufficiently different, there is not a suitable background in the portion of the target scene represented in the pixel to scatter light back to the camera, such as is represented in FIG. 4B. In such case, the camera can consider 282 such pixel to be an inoperable gas pixel, since there is likely insufficient scattering to properly perform a gas detection process.

In some embodiments, the camera can detect the presence of inoperable gas detection pixels by calculating a "sufficiency density" for a region of the image by determining the number of operable or inoperable gas detection pixels in that region. In regions where the sufficiency density of operable gas detection pixels is too low, the camera can treat each pixel in that region (even pixels sufficiently different from their corresponding pixels) as inoperable gas detection pixels. In one particular example, the camera can, for each pixel, determine the number of inoperable gas detection pixels among its nearest neighbor pixels. If the number of nearest neighbor pixels that are inoperable gas detection pixels exceeds a predetermined threshold, the pixel, or in some examples, the set of considered nearest neighbor pixels, is considered to be inoperable for performing a gas imaging process.

In some embodiments, a set of one or more pixels in an image can be compared to a corresponding set of one or more pixels in a corresponding portion of another image. For example, a set of one or more pixels in a first image can be averaged and compared to a corresponding set of one or more pixels in a second image. The averaged sets of one or more pixels can be compared in order to determine whether or not the one or more pixels are considered to be operational gas imaging pixels. In one example, the average value of one or more pixels in a first image is subtracted from an average value of a corresponding one or more pixels in a second image. If the average values are sufficiently different, each such pixel, or the one or more pixels, can be considered to be operable for performing a gas imaging process. It will be appreciated that other comparison techniques between sets of one or more pixels can be performed.

After considering the compared pixel to be either an operable or inoperable gas detection pixel, the camera can determine 284 if each of corresponding pixels to be compared have been compared. If not, the camera can move on to a next set of corresponding pixels and perform the same comparison 276. In various embodiments, the camera need not compare all possible corresponding pixels. For example, in some embodiments, the camera will only compare 276 corresponding pixels in portions of the target scene in which illumination from the light source can be detected, such as portion 268 in FIG. 5. Thus, the some configurations, the camera will compare 276 corresponding pixels from corresponding portions of the first and second images which need not include the entire first or second images. Accordingly, the step of determining 284 if each of the corresponding pixels has been compared can comprise determining if all corresponding pixels within certain corresponding portions of the first and second image have been compared. In general, corresponding portions comprising pixels to be compared can be defined in any of a variety of ways, such as all pixels likely to receive scattered light from the light source, all captured pixels, or any subset thereof.

Once all pixels have been compared, and all analyzed pixels are considered to be either operable or inoperable gas detection pixels, the camera can display 286 a gas detection image. The gas detection image can be such that pixels considered to be inoperable gas detection pixels are presented in a distinguishing way from pixels considered to be operable gas detection pixels. For example, with reference to FIG. 5, within portion 268 including visible light, infrared, and gas image data, pixels considered to be inoperable gas detection pixels can be presented as a solid color (e.g., gray, black, etc.) while pixels considered to be operable gas detection pixels are presented in the same way as pixels in portion 266 of the image including visible light and infrared image information. In another example, the camera can present pixels determined to be operable gas detection pixels including color visible light image data, while presenting pixels determined to be inoperable gas detection pixels in grayscale. While these are exemplary embodiments, it will be appreciated that many such examples exist within the display abilities of exemplary cameras according to various embodiments of the invention.

In displaying inoperable gas pixels in a distinguishing way from operable gas pixels as described, a user is able to clearly see in the image portions of the target scene in which gas imaging is more likely to be successfully performed. Similarly, the user will easily be able to tell which parts of the image are unlikely to provide reliable gas imaging functionality due to the lack of appropriate background. As such, the camera alerts the user of pixels in the target scene that are unsuitable for performing a gas imaging process.

In some embodiments, the camera is configured to alert the user if a certain number or percentage of possible pixels are unsuitable for performing a gas imaging process. In such embodiments, the camera can calculate the number of pixels determined to be unsuitable for performing a gas imaging process compared to the number of suitable pixels. If the number or percentage of such unsuitable pixels is sufficiently high, the camera can alert the user in one or more ways that there is an excess of inoperable gas detection pixels in the target scene. For example, if the number or percentage of unsuitable pixels crosses a threshold, the camera can display a message on the display 108 that the number of such pixels is too high. Additionally or alternatively, the camera can produce an alert tone to inform the user of an exceedingly high number of such pixels. In some embodiments, the camera can be configured to alert the user via sound or the display when the number or percentage of inoperable gas pixels crosses a threshold. In various embodiments, the threshold of number or percentage of pixels determined to be unsuitable in order to trigger an alert can be predetermined or defined by a user. In some further embodiments, the camera can emit an audible tone or pulse that changes with the number or percentage of pixels considered inoperable gas imaging pixels, continuously alerting the user.

In some embodiments, the process outlined in FIG. 6 can be repeated sequentially such that gas detection images can be generated and displayed in substantially real time. That is, the light sources can be pulsed in coordination with the capturing of the first and second images in order to repeatedly generate and display updated gas detection images. In such operation, a user can adjust the field of view of the camera and/or illumination sources and observe dynamically updating portions of the target area suitable for performing a gas imaging process. Accordingly, a user can adjust the camera while observing the gas detection image and position the camera in a location in which gas can be properly detected with the camera. The timing of such real-time operation can be controlled, for example, via processor 222.

Figure 7:
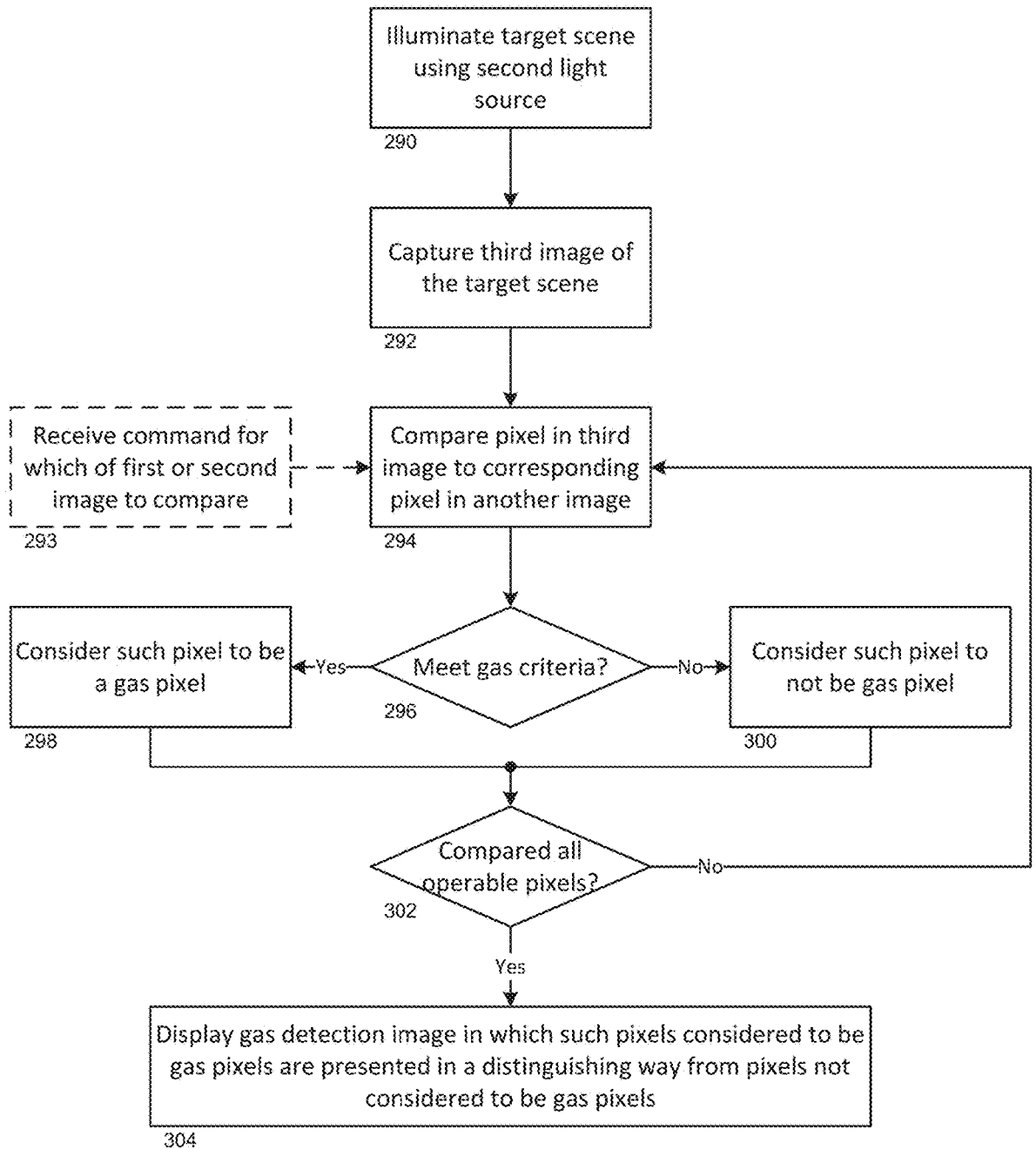
FIG. 7 is a process-flow diagram illustrating an exemplary gas imaging procedure according to some embodiments of the invention.

Upon determining which pixels in the target scene are suitable for performing a gas imaging process, that is, are operable gas detection pixels, the camera can perform a gas imaging procedure. FIG. 7 is a process-flow diagram illustrating an exemplary gas imaging procedure. In the process of FIG. 7, the camera can illuminate 290 the target scene using a second light source. The second light source can be configured to emit light at a second wavelength, which can be substantially absorbed by a target gas. Next, the camera can capture 292 a third image of the target scene while illuminating the scene via the second light source.

The camera can compare 294 pixels in the third image to corresponding pixels in another image, such as the first or second images as described with respect to FIG. 6. In some embodiments, the step of comparing 294 corresponding pixels in the third and another image is performed only on such pixels previously considered to be operable gas imaging pixels. After comparing a pair of corresponding pixels, the camera can determine 296 if one or more gas criteria are met. If so, the camera can consider 298 such a pixel to be a gas pixel, concluding that the pixel is representative of the target gas in the target scene. If, however, the pixel is deemed to have not met the gas criteria, the camera can consider 300 such pixel to not be a gas pixel, i.e., not representative of the target gas in the target scene.

After determining 296 if a pixel is considered to be a gas pixel, the camera can determine 302 if all operable gas pixels in the third image, for example pixels in the third image corresponding to pixels considered to be operable gas pixels in the process of FIG. 6, have been compared. If not, a new pixel is compared 294. Once all operable gas imaging pixels have been analyzed, the camera can generate and display 304 a gas detection image in which such pixels considered to be gas pixels are presented in a distinguishing way from pixels not considered to be gas pixels. Thus, the camera can determine which pixels in the gas detection image are representative of the target gas in the target scene, and present such pixels to a user in a distinguishing way from pixels not considered to be gas pixels. This can assist a user in performing a gas imaging operation, and in detecting a target gas in a target scene.

As described with respect to FIG. 6, the process illustrated in FIG. 7 can be performed repeatedly in order to generate such gas detection images in real time. In doing so, a user can quickly and easily inspect a large area for a target gas by sweeping the field of view of the camera across the area and watching for detected gas pixels to be displayed in the gas detection image. In some embodiments, the process of FIGS. 6 and 7 can be combined in order to generate and display a gas detection image in which inoperable gas detection pixels are presented in a distinguishing way from operable gas detection pixels, and furthermore, of the operable gas detection pixels, those considered to be gas pixels are presented in a further distinguishing way from those not considered to be gas pixels In some embodiments, first and/or second light sources do not illuminate the entire target scene captured by the camera. Accordingly, in some embodiments, the step of illuminating 272 the target scene using a first light source from the method outlined in FIG. 6 can comprise illuminating a first portion of the target scene. Similarly, the step of illuminating 290 the target scene using the second light source from the method outlined in FIG. 7 can comprise illuminating a second portion of the target scene. In embodiments in which the methods of FIGS. 6 and 7 are performed together, the first and second portions of the target scene can at least partially overlap. Thus, in the overlapping regions, pixels already considered to be operable gas detection pixels can be compared to the gas criteria and considered to either be or not be gas pixels. In some embodiments, the first and second portions of the target scene are substantially the same.

Figure 8:
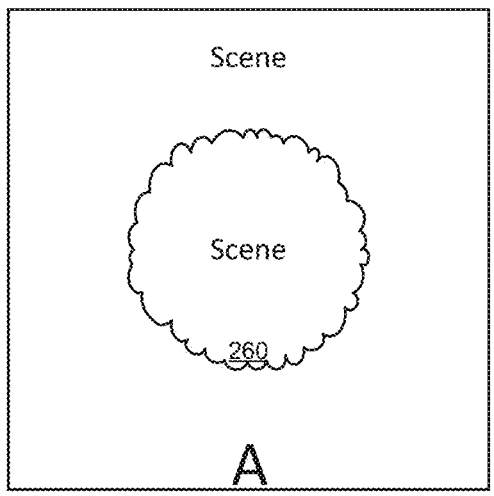
FIG. 8 shows a series of captured scenes and results of exemplary operations performed on such scenes according to some embodiments of the invention.
Figure 8:
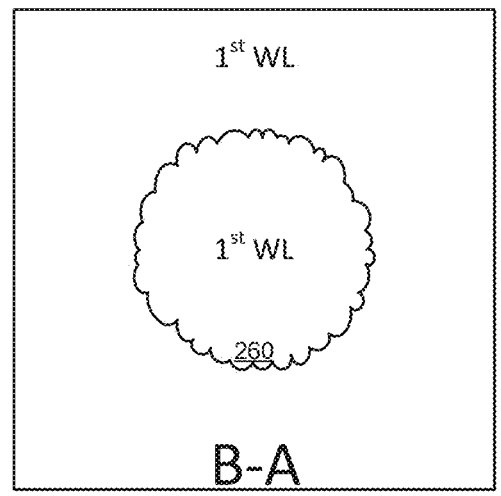
Figure 8:
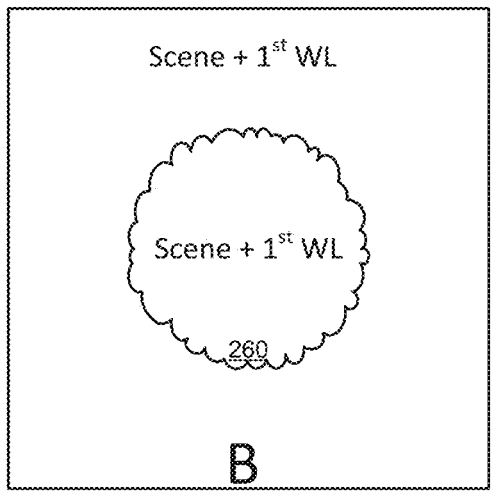
Figure 8:
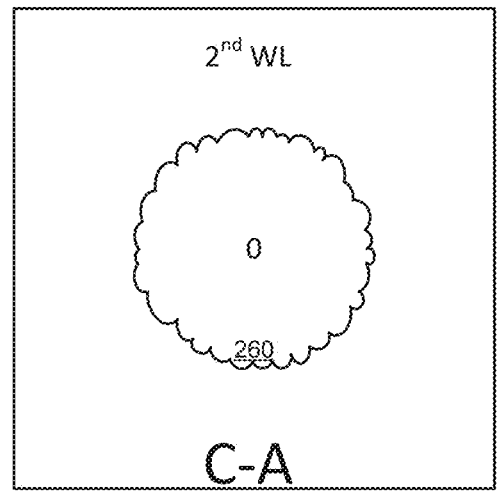
Figure 8:
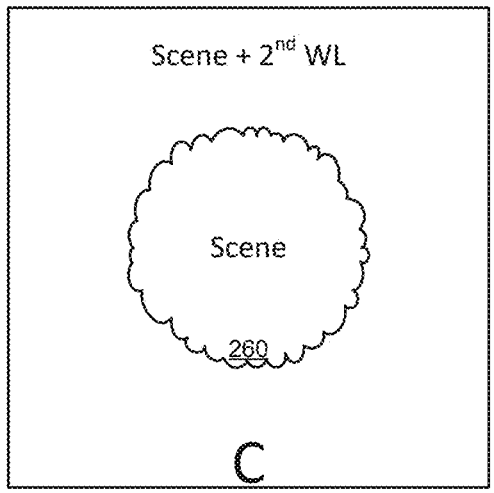
Figure 8:
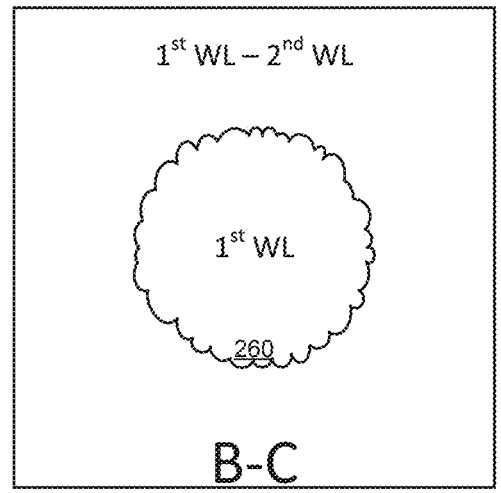

As mentioned, in the process illustrated in FIG. 7, a pixel in the third image can be compared to a corresponding pixel in another image, such as the first or second images as described with reference to FIG. 6. Determining 296 whether or not such a pixel meets one or more gas criteria can depend on which comparison is used. FIG. 8 illustrates a series of captured images A, B and C of a target scene including target gas 260, along with a set of image comparisons. Image A represents the target scene without any illumination from a light source. Image B represents the second image of the target scene while illuminated with light of the first wavelength via the first light source. Because light of the first wavelength is not significantly absorbed by the target gas, it is detected in areas of the image with and without the presence of the target gas. Image C represents the third image of the target scene while illuminated with light of the second wavelength from the second light source. Because light of the second wavelength is substantially absorbed by the target gas 260, portions of the target scene comprising the target gas 260 will show less scattered light of the second wavelength when compared to portions of the target scene not comprising the target gas 260. Portions of the target scene not comprising the target gas will, by comparison, show unattenuated scattered light of the second wavelength along with the target scene. In some imaging situations, portions of the target scene comprising the target gas will attenuate the light of the second wavelength to varying degrees, depending, for example, on the amount of gas encountered by the light and the absorption spectrum of the target gas. Accordingly, in some cases, the appearance of the target gas in a target scene can appear similar to dynamic smoke or a shadow with time-varying shape, position and intensity.

In some embodiments, a camera can simply present the third image (C) to the user on a display, whereby the user can observe where in the image the light of the second wavelength does not appear, or appears attenuated, and can presume such portions of the target scene to comprise the target gas. Often, because gas in the target scene is typically not stationary with time, movement (e.g., swirling) of attenuated portions of the target scene are easily observed by the user. However, in some situations, because target scenes can be variable and, particularly in the case of infrared imaging, unknown prior to imaging, it can be difficult to differentiate light of the second wavelength from portions of the target scene that may have a similar appearance. In such instances, comparing the third image to either the first or second images as in step 294 in FIG. 7 and as illustrated in portions of FIG. 8 can provide a more definitive representation of the target gas in the target scene.

Box C-A in FIG. 8 demonstrates a simple subtraction of the first image (no illumination) from the third image (illumination with the second wavelength). As shown, the resulting image comprises the second wavelength in the area in which the target gas 260 is not present to absorb the second wavelength, and is substantially canceled out in the portions of the image representative of the target gas 260 in the target scene. Accordingly, no portion of the resulting image is scene dependent, allowing for a more objective determination of where there is gas in the image. In such a situation, the camera can compare each resulting pixel to a threshold, wherein pixels whose value is below the threshold is considered to be gas pixels, while pixels whose value is above the threshold is considered to not be gas pixels, and can be presented accordingly. In the context of FIG. 7, a pixel resulting from such calculation being below the threshold can be considered to meet the gas criteria as in 296.

Box B-C in FIG. 8 demonstrates an alternative comparison, this time between the second image (illumination with the first wavelength) and the third image. The resulting image comprises a measurement of the first wavelength within any areas of the scene representative of the target gas 260 and the difference between the measured first wavelength and measured second wavelength in areas not representative of the target gas 260. In this example, the resulting image is also independent of the scene and includes information regarding only the emitted first and second wavelengths of light. The camera can then compare each resulting pixel to a threshold as described above, however, in this case, pixels above the threshold can be considered to be gas pixels, while pixels below the threshold can be considered to be not gas pixels.

As illustrated by the examples in boxes C-A and B-C in FIG. 8, a step of comparing 294 a pixel in the third image to a corresponding pixel in another image can include performing a subtraction, and can further include comparisons with the first or the second image. In each case, determining 296 if a pixel meets gas criteria can include comparing the subtracted result to a threshold. As shown and described, a pixel can be considered a gas pixel if it is above or below the threshold, depending on the nature of the pixel comparison. While the several described examples illustrate comparison by subtraction, it will be appreciated that various forms of image combination can be applied, such as multiplication, for example.

In some embodiments, a series of images can be averaged to create an aggregate image to be used in various image comparisons and combinations as described herein. For example, a camera can capture a plurality of images of a target scene while the target scene is illuminated with the first or second light source. Such plurality of images can undergo an averaging process to create a resultant second or third image to be used in the processes herein described. Various averaging processes can be used. For example, in some embodiments, a rolling or weighted average of a number of consecutive frames can be calculated. In further processes, such a rolling or weighted average can be performed of a number of previously captured images, and subsequently subtracted from a present image. Such a technique can accentuate visualization of a moving target gas when compared to a relatively stationary background image. In some such embodiments, the resulting averaged image can be presented in conjunction with a portion of the entire image. For example, an averaging technique can be performed on some subset of pixels of the entire image, and subsequently overlaid (e.g., a picture-in-picture relationship) or blended with another image, for example a visible light image. In an exemplary embodiment, with reference to FIG. 5, an averaging technique can be performed in only portion 268 of the image, and presented within an entirely VL image (e.g., portion 264) and/or VL+IR blended image (e.g., portion 266). Such presentation configurations can provide a user with a significant portion of the background scene so as to provide context of the averaged portion of the scene.

As described herein, in various embodiments of the invention, a camera can utilize one or more light sources to determine which portions of a target scene are suitable for performing a gas imaging process (i.e., comprise operable gas imaging pixels) and which portions are unsuitable (i.e., comprise inoperable gas detection pixels). Moreover, the camera can determine, among operable gas imaging pixels, which of the pixels are representative of a target gas in the target scene. The camera can display a gas detection image in which one or more of gas pixels, operable gas pixels and inoperable gas pixels can be displayed in a distinguishing manner from the others so as to be easily viewed and distinguished by a user. The camera can display such images in substantially real time, further allowing a user to quickly survey a large area and determine where gas imaging is likely possible and, in some embodiments, where a target gas is present in the target scene.

Displaying certain pixels in a distinguishing manner can be done in any of several ways. For example, inoperable gas detection pixels and/or detected gas pixels can be replaced with pixels of a solid, distinct color. In some exemplary embodiments, inoperable gas detection pixels can be displayed as a "blanked out" color such as gray, purple, black or white. Additionally or alternatively, regions of inoperable gas detection pixels can be outlined and/or flashed to alert the user of the presence of such pixels. Detected gas pixels might be displayed in a salient color when compared to most backgrounds, such as a lime green.

In some examples, a camera can include visible light and infrared camera modules as described above. In such embodiments, a camera can capture first, second and third infrared images (corresponding to various illumination configurations) and a visible light image of substantially the same scene. Processes herein described can be performed in order to detect operable and/or inoperable gas detection pixels and, in some embodiments, gas pixels. Such information can be presented to a user utilizing visible light pixels, infrared pixels, operable and/or inoperable gas detection pixels and gas pixels in a variety of display configurations. For example, a gas detection image similar to the image of FIG. 5 can comprise either a color or black and white visible light image in the outer portion of the image 264. In a picture-in-picture type arrangement, a combination visible light and infrared representation of the target scene can be presented in portion 266 of the image. Infrared image data can be palettized in order to represent infrared data in an observable way. Any appropriate palettization techniques can be used, and in some examples, visible light image data can be combined with the infrared image to provide additional context for an observer.

Within the portion 266 of the image comprising infrared image information, portion 268 can represent portions of the image in which light emitted from first and/or second light sources and scattered back to the camera can be detected. Accordingly, in the exemplary embodiment, within portion 268 of the image, the camera can detect and display inoperable gas detection pixels, alerting a viewer of such pixels. Inoperable gas detection pixels can be presented within portion 268 of the image in a manner which is generally distinguishable from the operable gas detection pixels. For example, in some configurations, operable gas detection pixels within portion 268 are generally presented as pixels including palettized infrared image data. Inoperable gas detection pixels can then be presented in a color or shade that is not within the palettization scheme of the infrared image, thereby clearly distinguishing such pixels from the operable gas imaging pixels when presented to a viewer. In some embodiments, the camera can further detect which of the operable gas detection pixels represent the target gas in portion 268 of the target scene, and present such pixels in a manner distinguishable from both the palettized infrared image data and the inoperable gas detection pixels.

Example thermal image cameras and related techniques have been described. The techniques described in this disclosure may also be embodied or encoded in a computer-readable medium, such as a non-transitory computer-readable storage medium containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), a hard disk, optical media, or other computer readable media.

Various embodiments have been described. Such examples are non-limiting, and do not define or limit the scope of the invention in any way. Rather, these and other examples are within the scope of the following claims.

The invention claimed is:

1. A system comprising:
a camera module comprising a lens assembly having an associated sensor for detecting images of a target scene;
a display; and
a processor in communication with the camera module and the display and being configured to:
capture a first image of a target scene, the first image comprising a plurality of regions;
compare each the plurality of regions in the captured first image to a corresponding region in a second image, the second image having been previously captured;
determine which of the plurality of regions in the first image are unsuitable for performing a gas imaging process of a target gas based on the comparison; and
alert a user of the presence of such unsuitable regions in the target scene.

2. The system of claim 1, further comprising a first light source capable of emitting light at a first wavelength, the first wavelength not being an absorption wavelength of the target gas; and wherein
the sensor of the camera module is sensitive to a range of wavelengths of light including the first wavelength.

3. The system of claim 2, wherein the processor is configured to cause the first light source to illuminate the target scene; wherein
the capturing the first image of the target scene is performed while the scene is illuminated via the first light source; and
the second image represents the target scene while the scene is not illuminated via the first light source.

4. The system of claim 3, further comprising a second light source capable of emitting light at a second wavelength different from the first, the second wavelength being an absorption wavelength of the target gas; and wherein
the processor is further configured to capture a third image of the target scene while the scene is illuminated via the second light source; and
compare the third image to the second image to determine regions in the target scene in which the target gas is present.

5. The system of claim 1, wherein the alerting a user of the presence of unsuitable regions in the target scene comprises displaying a gas detection image representing the target scene on the display, wherein regions representing determined to be unsuitable for performing the gas imaging process are presented in a distinguishing way from regions suitable for performing the gas imaging process.

6. The system of claim 5, wherein
the processor is further configured to perform a gas detection process to determine regions in which a gas is present in the target scene; and
regions in the gas detection image corresponding to those in which the gas is determined to be present are presented in a further distinguishing way from regions in which gas is not determined to be present and from regions determined to be unsuitable for performing the gas imaging process.

7. The system of claim 5, wherein each of the plurality of regions in the first image represents a single pixel in the first image, and wherein pixels determined to be unsuitable for performing the gas imaging process are presented in a distinguishing way from pixels suitable for performing the gas imaging process.

8. The system of claim 1, wherein the camera module comprises an infrared camera module comprising an infrared sensor array.

9. The system of claim 8, wherein the infrared camera module, the display, and the processor are integrated into a handheld infrared camera.

10. The system of claim 9, wherein the handheld infrared camera further comprises a visible light camera module.

11. A method for generating a gas image comprising:
receiving a first image of a target scene, the first image comprising a plurality of regions;
receiving a second image of the target scene, the second image comprising a plurality of regions, each of the plurality of regions in the second image corresponding to a region in the first image;
comparing corresponding regions the received first image and the received second image to determine which of the plurality of regions is suitable for performing a gas imaging process; and
generating a display image including a plurality of regions, each of the regions in the display image corresponding to one of the regions in the first image, wherein regions in the display image corresponding to regions determined to be unsuitable for performing the gas imaging process are presented in a distinguishing way from regions in the display image corresponding to regions not determined to be unsuitable for performing the gas imaging process.

12. The method of claim 11, further comprising:
receiving a third image of the target scene, the third image comprising a plurality of regions, each of the plurality of regions in the third image corresponding to a region in the first image; and
comparing corresponding regions in the received first image and the received third image to determine which of the plurality of regions include a gas present in the target scene.

13. The method of claim 12, wherein
regions in the display image that both:
(a) correspond to regions that are not determined to be unsuitable for performing the gas imaging process; and
(b) correspond to regions in which it is determined that the gas is present in the target scene
are presented in a distinguishing way from the regions that:
(c) correspond to regions that are determined to be unsuitable for performing the gas imaging process; and
(d) correspond to regions that are not determined to be unsuitable for performing the gas imaging process and in which it is not determined that gas is present in the target scene.

14. The method of claim 12, wherein comparing corresponding regions in the received first image and the received third image comprises comparing only regions corresponding to those not determined to be unsuitable for performing the gas imaging process.

15. The method of claim 12, wherein the second image of the target scene represents the target scene illuminated via a first light source and the first image of the target scene represents the target scene not illuminated via the light source.

16. The method of claim 15, wherein the third image of the target scene represents the target scene illuminated via a second light source, different from the first.

17. The method of claim 11, wherein
comparing corresponding regions the received first image and the received second image comprises determining, for each region, whether or not a difference between corresponding regions in the first image and the second image is greater than a predetermined threshold; and a region is determined to be suitable for performing a gas imaging process if the difference is greater than the predetermined threshold.

18. The method of claim 11, wherein each of the plurality of regions consists of a single pixel.

* * * * *